(12) United States Patent
Batchelor et al.

(10) Patent No.: US 11,547,467 B2
(45) Date of Patent: Jan. 10, 2023

(54) ADVANCED ENERGY DEVICE WITH BIPOLAR DISSECTION CAPABILITY

(71) Applicant: GYRUS ACMI, INC., Southborough, MA (US)

(72) Inventors: Kester J. Batchelor, Mound, MN (US); Huisun Wang, Maple Grove, MN (US); Riyad Moe, Madison, WI (US)

(73) Assignee: Gyrus ACMI, Inc., Westborough, MA (US)

( * ) Notice: Subject to any disclaimer, the term of this patent is extended or adjusted under 35 U.S.C. 154(b) by 379 days.

(21) Appl. No.: 15/781,735

(22) PCT Filed: Jan. 11, 2016

(86) PCT No.: PCT/US2016/012823
§ 371 (c)(1),
(2) Date: Jun. 6, 2018

(87) PCT Pub. No.: WO2017/123189
PCT Pub. Date: Jul. 20, 2017

(65) Prior Publication Data
US 2018/0360525 A1 Dec. 20, 2018

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00083* (2013.01);
(Continued)

(58) Field of Classification Search
CPC ...... A61B 18/1445; A61B 2018/00083; A61B 2018/00077; A61B 2018/00607;
(Continued)

(56) References Cited

U.S. PATENT DOCUMENTS 5,269,780 A 12/1993 Roos
5,445,638 A 8/1995 Rydell et al.
(Continued)

FOREIGN PATENT DOCUMENTS

EP 1287788 A1 3/2003
EP 1330991 A1 7/2003
(Continued)

OTHER PUBLICATIONS

Search Report and Written opinion for International Application No. PCT/US2016/012823; dated Nov. 7, 2016.
(Continued)

*Primary Examiner* — Jaymi E Della
(74) *Attorney, Agent, or Firm* — Schwegman Lundberg & Woessner, P.A.

(57) ABSTRACT

A medical device is disclosed. The medical device comprises a bipolar forceps including a jaw assembly. The jaw assembly comprises a first jaw body; a second jaw body; and a sealing plate. A therapy current can be passed between the sealing plate and the first jaw body. The therapy current can be restricted from passing between the first jaw body and the second jaw body. The therapy current can be restricted from passing between the sealing plate and the second jaw body.

18 Claims, 6 Drawing Sheets

(52) U.S. Cl.
CPC .............. *A61B 2018/00607* (2013.01); *A61B 2018/1452* (2013.01); *A61B 2018/1455* (2013.01)

(58) Field of Classification Search
CPC .... A61B 2018/0063; A61B 2018/1452; A61B 2018/1455
See application file for complete search history.

(56) References Cited

U.S. PATENT DOCUMENTS

| | | | |
|---|---|---|---|
| 5,458,598 A | 10/1995 | Feinberg et al. | |
| 5,766,166 A | 1/1998 | Hooven | |
| 5,735,849 A | 4/1998 | Baden et al. | |
| 5,908,420 A | 6/1999 | Parins et al. | |
| 5,951,549 A | 9/1999 | Richardson et al. | |
| 5,951,551 A | 9/1999 | Erlich | |
| 6,086,586 A | 7/2000 | Hooven | |
| 6,113,596 A | 9/2000 | Hooven et al. | |
| 6,152,923 A | 11/2000 | Ryan | |
| 6,190,386 B1 | 2/2001 | Rydell | |
| 6,270,497 B1 | 8/2001 | Sekino et al. | |
| 6,273,887 B1* | 8/2001 | Yamauchi | A61B 18/1445 606/51 |
| 6,334,860 B1 | 1/2002 | Dorn | |
| 6,447,511 B1 | 9/2002 | Slater | |
| 6,676,660 B2 | 1/2004 | Wampler et al. | |
| 6,679,882 B1 | 1/2004 | Kornerup | |
| 6,929,641 B2 | 8/2005 | Goble et al. | |
| 6,966,907 B2 | 11/2005 | Goble | |
| 6,984,231 B2 | 1/2006 | Goble et al. | |
| 7,147,637 B2* | 12/2006 | Goble | A61B 18/1442 606/50 |
| 7,204,835 B2 | 4/2007 | Latterell et al. | |
| 7,208,005 B2 | 4/2007 | Frecker et al. | |
| 7,232,440 B2 | 6/2007 | Dumbauld et al. | |
| 7,442,194 B2 | 10/2008 | Dumbauld et al. | |
| 8,257,352 B2 | 9/2012 | Lawes et al. | |
| 8,262,655 B2 | 9/2012 | Ghabrial et al. | |
| 8,273,085 B2 | 9/2012 | Park et al. | |
| 8,597,296 B2 | 12/2013 | Lawes et al. | |
| 10,413,350 B2 | 9/2019 | Batchelor et al. | |
| 2002/0188294 A1* | 12/2002 | Couture | A61B 18/1445 606/171 |
| 2003/0073990 A1 | 4/2003 | Goble et al. | |
| 2003/0109876 A1* | 6/2003 | Yamauchi | A61B 18/1442 606/48 |
| 2003/0163123 A1 | 8/2003 | Goble et al. | |
| 2004/0122423 A1 | 6/2004 | Dycus et al. | |
| 2005/0113826 A1 | 5/2005 | Johnson et al. | |
| 2006/0020265 A1 | 1/2006 | Ryan | |
| 2006/0084973 A1 | 4/2006 | Hushka | |
| 2006/0224158 A1* | 10/2006 | Odom | A61B 18/1445 606/171 |
| 2006/0271038 A1 | 11/2006 | Johnson et al. | |
| 2008/0015575 A1* | 1/2008 | Odom | A61B 18/1445 606/51 |
| 2008/0045947 A1 | 2/2008 | Johnson et al. | |
| 2010/0036371 A1* | 2/2010 | Park | A61B 18/1445 606/33 |
| 2011/0046623 A1 | 2/2011 | Reschke | |
| 2011/0319886 A1 | 12/2011 | Chojin et al. | |
| 2012/0323238 A1* | 12/2012 | Tyrrell | A61B 17/285 606/52 |
| 2013/0018411 A1 | 1/2013 | Collings et al. | |
| 2013/0123837 A1 | 5/2013 | Roy et al. | |
| 2014/0100568 A1* | 4/2014 | Garrison | A61B 18/1445 606/45 |
| 2014/0276794 A1 | 9/2014 | Batchelor et al. | |
| 2014/0288541 A1* | 9/2014 | Eshkol | A61B 17/32056 606/7 |
| 2014/0288553 A1* | 9/2014 | Johnson | A61B 18/1445 606/42 |
| 2015/0088128 A1* | 3/2015 | Couture | A61B 18/1445 606/42 |
| 2015/0137422 A1 | 5/2015 | Horner et al. | |
| 2019/0021785 A1 | 1/2019 | Batchelor et al. | |
| 2021/0038287 A1 | 2/2021 | Batchelor et al. | |

FOREIGN PATENT DOCUMENTS

| | | |
|---|---|---|
| EP | 3386408 A1 | 10/2018 |
| EP | 3389533 A1 | 10/2018 |
| EP | 3389533 B1 | 10/2019 |
| EP | 3603555 A1 | 2/2020 |
| WO | WO-2004032777 A1 | 4/2004 |
| WO | 2015/047611 A1 | 4/2015 |
| WO | WO-2017123189 A1 | 7/2017 |
| WO | WO-2017123468 A1 | 7/2017 |

OTHER PUBLICATIONS

"U.S. Appl. No. 16/068,753, Non Final Office Action dated Feb. 15, 2019", 14 pgs.
"U.S. Appl. No. 16/068,753, Notice of Allowance dated May 22, 2019", 12 pgs.
"U.S. Appl. No. 16/068,753, Preliminary Amendment filed Jul. 9, 2018", 6 pgs.
"U.S. Appl. No. 16/068,753, Response filed May 8, 2019 to Non Final Office Action dated Feb. 15, 2019", 14 pgs.
"U.S. Appl. No. 16/534,047, Preliminary Amendment filed Aug. 7, 2019", 6 pgs.
"European Application Serial No. 17701938.7, Communication Pursuant to Article 94(3) EPC dated Jan. 24, 2019", 4 pgs.
"European Application Serial No. 17701938.7, Intention to Grant dated Jul. 8, 2019", 33 pgs.
"European Application Serial No. 17701938.7, Response filed Apr. 10, 2019 to Communication Pursuant to Article 94(3) EPC dated Jan. 24, 2019", 30 pgs.
"European Application Serial No. 19191726.9, Extended European Search Report dated Jan. 7, 2020", 8 pgs.
"European Application Serial No. 19191726.9, Response filed Aug. 5, 2020 to Extended European Search Report dated Jan. 7, 2020", 9 pgs.
"International Application Serial No. PCT/US2016/012823, International Preliminary Report on Patentability dated Jul. 26, 2018", 18 pgs.
"International Application Serial No. PCT/US2017/012504, International Preliminary Report on Patentability dated Jul. 26, 2018", 16 pgs.
"International Application Serial No. PCT/US2017/012504, International Search Report dated May 18, 2017", 4 pgs.
"International Application Serial No. PCT/US2017/012504, Written Opinion dated May 18, 2017", 14 pgs.
"European Application Serial No. 19191726.9, Extended European Search Report dated Jan. 7, 2020", 7 pgs.
"U.S. Appl. No. 16/534,047, Non Final Office Action dated Feb. 11, 2022", 13 pgs.
"U.S. Appl. No. 16/534,047, Response filed May 11, 2022 to Non Final Office Action dated Feb. 11, 2022", 16 pgs.
"European Application Serial No. 16705329.7, Communication pursuant to Rule 164(2) EPC dated Dec. 10, 2021", 7 pgs.
"U.S. Appl. No. 16/534,047, Notice of Allowance dated Aug. 15, 2022", 13 pgs.
"European Application Serial No. 16705329.7, Notification Regarding Rule 164 and Article 94(3) EPC dated Apr. 7, 2022", 13 pgs.
"European Application Serial No. 16705329.7, Response filed Aug. 15, 2022 to Notification Regarding Rule 164 and Article 94(3) EPC dated Apr. 7, 2022", 8 pgs.

* cited by examiner

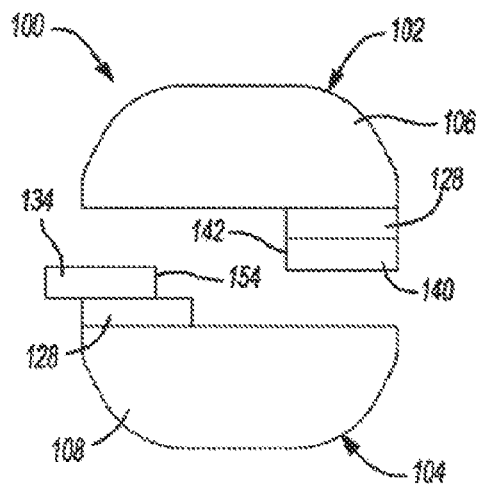 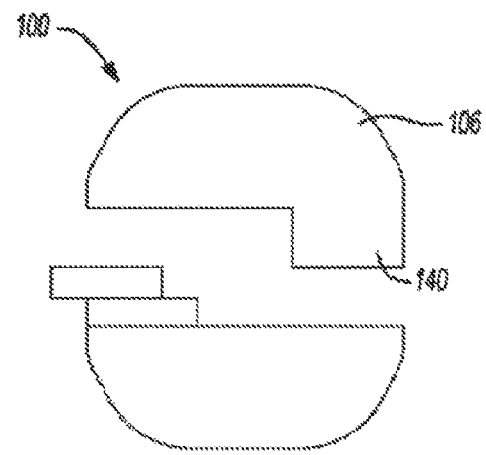
Fig-12A    Fig-12B
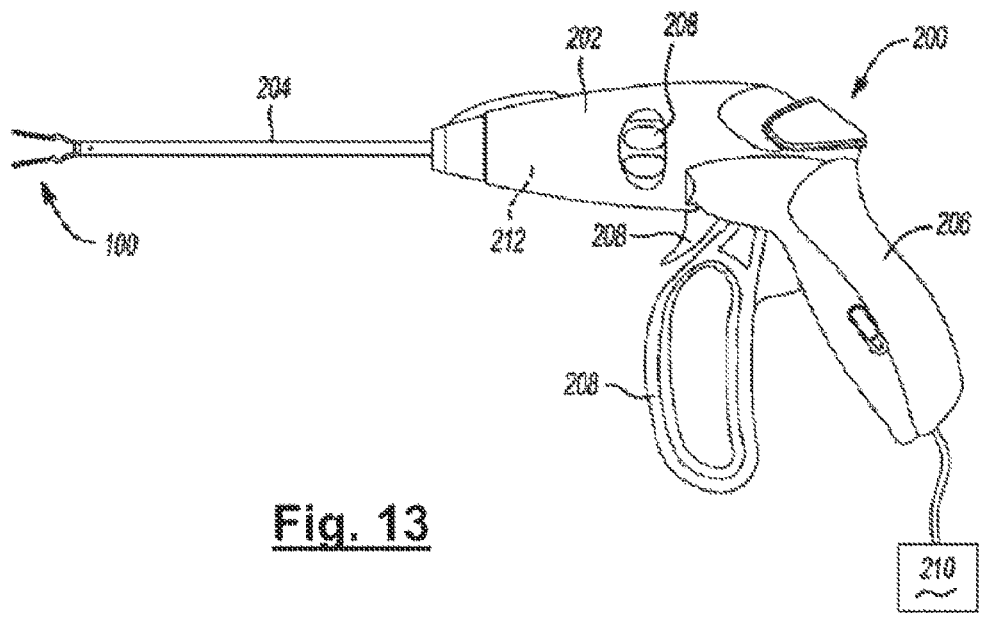
Fig. 13

ADVANCED ENERGY DEVICE WITH BIPOLAR DISSECTION CAPABILITY

FIELD

These teachings relate generally to medical devices, and more particularly to electrosurgical devices for effecting an anatomical feature.

BACKGROUND

A forceps is a plier-like device that includes a jaw assembly for effecting azo anatomical feature. For example, a forceps can be used to grip, capture, grasp, manipulate, pull, constrict, cut, and/or dissect an anatomical feature such as a vessel or tissue. Some forceps also include electrosurgical capabilities so that anatomical feature can be cut and/or coagulated with one or more therapy currents.

Some forceps can be used to cut or dissect an anatomical feature via one or more blunt dissection techniques. One blunt dissection technique is sweep dissection. In sweep dissection, the jaw assembly, or a portion of the jaw assembly, such as an edge, is moved or "swept" across the anatomical feature thereby cutting or dissecting the anatomical feature.

Opportunities exist for improving such devices. For example, it may be desirable to have a medical device for effectively coagulating, cutting, and/or dissecting an object or anatomical feature between the jaws, and also for effectively cutting or dissecting an anatomical feature via sweep dissection. Some examples of known medical devices are disclosed in U.S. Pat. Nos. 8,262,655, 8,273,085, and 6,676,660; U.S. Patent Application Publication Numbers 2014/0276794, 2014/0100568, and 2008/0045947; and in WO 2015/047611, the disclosures of which are hereby incorporated by reference in their entirety.

SUMMARY

Disclosed is a medical device. The medical device comprises a bipolar forceps including a jaw assembly. The jaw assembly comprises a first jaw body; a second jaw body; and a sealing plate. A therapy current can be passed between the sealing plate and the first jaw body. The therapy current can be restricted from passing between the first jaw body and the second jaw body. The therapy current can be restricted from passing between the sealing plate and the second jaw body.

A medical device is disclosed, comprising a bipolar forceps including a jaw assembly that is moveable between a closed position and an open position. The jaw assembly comprises a first jaw body; a second jaw body; and sealing plate. In the closed position, the first jaw body has a first polarity and the sealing plate has an opposing second polarity. In the closed position, at least a portion of the first jaw body contacts at least a portion of the second jaw body so that the first jaw body and the second jaw body are in electrical communication and both have the first polarity. In the open position, the first jaw body and the second jaw body are electrically isolated from each other and free from contacting each other.

A medical device is disclosed, comprising a bipolar forceps including a jaw assembly. The jaw assembly comprises a first jaw and a second jaw. The first jaw comprises a first jaw body; an insulator; and sealing plate. The second jaw body comprises a second jaw body. The first jaw body and the sealing plate are electrically isolated from one another via the insulator. In a first use state, an anatomical feature is surgically effected between the sealing plate and the second jaw body by passing a therapy current between the sealing plate and the second jaw body. In a second use state, an anatomical feature is surgically elected by contacting the anatomical feature with an edge of the sealing plate and passing a therapy current between the sealing plate and both the first jaw body and the second jaw body.

A medical device is disclosed, comprising a bipolar forceps including a jaw assembly. The jaw assembly comprises a first jaw and a second jaw. The first jaw comprises a first jaw body; a sealing plate; and an insulator electrically isolating the first jaw body from the sealing plate. The second jaw comprises a second jaw body. In a first use state, an anatomical feature is surgically effected between the sealing plate and the second jaw body by passing a therapy current between the sealing plate and the second jaw body. In a second use state an anatomical feature is surgically affected by contacting the anatomical feature with an edge of the sealing plate and passing a therapy current between the sealing plate and both the first jaw body and the second jaw body, or between the first jaw body and the second jaw body.

A medical device is disclosed, comprising a bipolar forceps including a jaw assembly. The jaw assembly comprises a first jaw and a second jaw. The first jaw comprises a first jaw body; a first sealing plate; and a first insulator electrically isolating the first jaw body and the first sealing plate. The second jaw body comprises a second jaw body; a second sealing plate; and second insulator electrically isolating the second jaw body and the second sealing plate. In a first use state, the first sealing plate and the second sealing plate have opposing polarities so that an anatomical feature is surgically effected between the first sealing plate and the second, sealing plate. In a second use state, the first sealing plate has a polarity that is opposite a polarity of the first jaw body and the second jaw body so that an anatomical feature is surgically effected with an edge of the first sealing plate. The medical device includes one or more of the following: a profile of the first sealing plate or a profile of the second sealing plate is located within a profile of the first jaw body or a profile of the second jaw body; the profile of the second sealing plate is located within the profile of the first sealing plate; in the first use state, both the first jaw body and the second jaw body have a polarity that is the same as a polarity of the second sealing plate; at least a portion of the first sealing plate is reconfigurable so that the edge of the first sealing plate substantially matches an edge of the second sealing plate, or the edge of the first sealing plate is made to extend beyond the edge of the second sealing plate; in the second use state, the second sealing plate has a polarity that is the same as a polarity of both the first jaw body and the second jaw body; and in the second use state a polarity of the second sealing plate is the same as the polarity of the first sealing plate.

A medical device is disclosed, comprising a bipolar forceps including a jaw assembly. The jaw assembly comprises a first jaw and a second jaw. The first jaw comprises a first jaw body; a first electrode having a first lateral edge and a second lateral edge. The second jaw body comprises a second jaw body; a sealing plate including a first lateral edge and a first interior edge; and an insulating layer electrically isolating the second jaw body from sealing plate. The first lateral edge of the sealing plate extends beyond a first side edge of the second jaw body. The first electrode is laterally located relative to the sealing plate. A gap is defined between the first lateral edge of the first electrode and the first interior edge of the sealing plate. In a first electrosurgical form, the sealing plate has a polarity that opposes a polarity of the first jaw body so that an anatomical feature is surgically effected between the electrode and the sealing plate. In a second electrosurgical form, the sealing plate has a polarity that opposes the polarity of the first jaw body and a polarity of the second jaw body so that an anatomical feature is surgically effected with the first lateral edge of the sealing plate.

BRIEF DESCRIPTION OF THE DRAWINGS

FIG. 12A is a sass-sectional view of a jaw assembly.
FIG. 12B is a cross-sectional view of a jaw assembly.
FIG. 13 is a side view of a medial device including the jaw assembly described herein.

DETAILED DESCRIPTION

Figure 1:
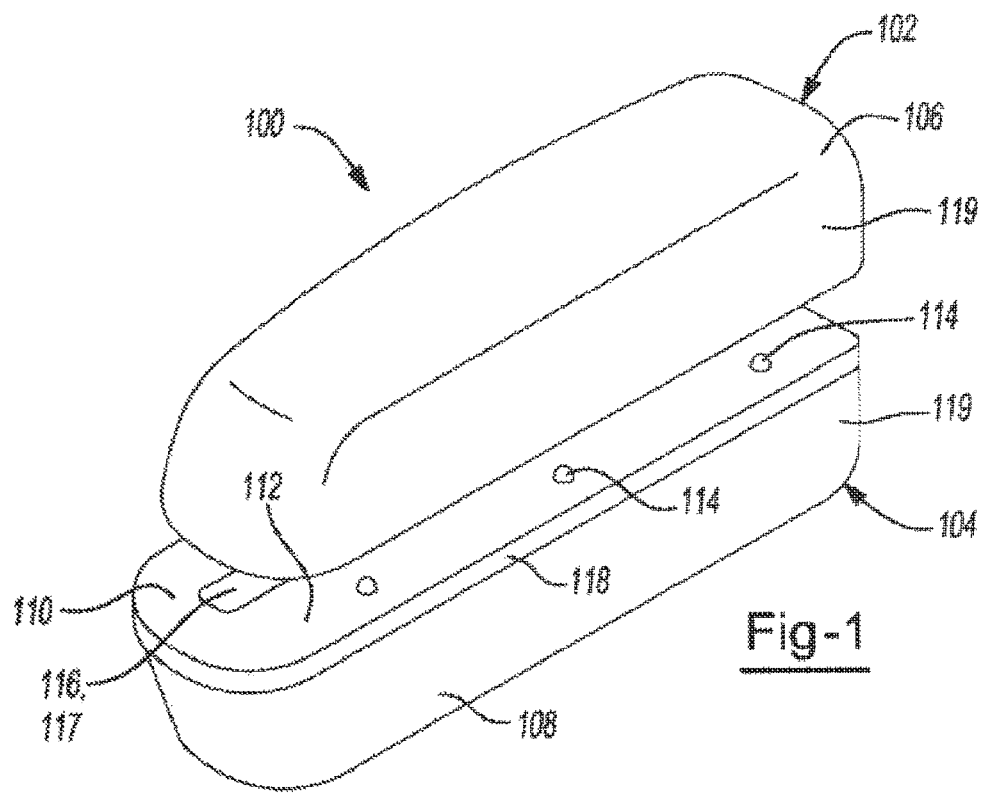
FIG. 1 is a perspective view of a jaw assembly.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide a medical device. The medical device can be any device for effecting an object or anatomical feature. Effecting may mean, for example, manipulating, engaging, moving, grasping, gripping, constricting, pushing, pulling, cutting, tearing, coagulating, sealing, cauterizing, dissecting, fulgurating, the like, or a combination thereof an object or anatomical feature. The anatomical feature may be any anatomical feature, such as a vessel, tissue, vein, artery, the like, or a combination thereof. The medical device can be used in virtually any medical procedure. The medical device can be used in open procedures, laparoscopic procedures, or both. The medical device may be any device having jaws, or a jaw assembly. The medical device can be a medical forceps. The medical device can be a bipolar forceps. The medical device operates as bipolar coagulating forceps and a bipolar dissector.

The medical device can be used with or without power. When used with power, one or more electrical currents, therapies, and/or signals may be provided to the medical device. The one or more electrical currents, therapies, and/or signals may be provided to, through, and/or between the jaw assembly, the one or more jaws, the one or more jaw bodies, the one or more sealing plates, the one or more electrodes, the one or more cutting elements, a remote pad or electrode, or a combination thereof. The one or more electrical currents, therapies, and/or signals may be provided to, through, and/or between the jaw assembly, and/or the features of the jaw assembly so that an object or anatomical feature in contact and/or contacted by the jaw assembly and/or the one or more features of the jaw assembly can be electrically effected.

One or more power sources may provide the one or more electrical currents, therapies, and/or signals. The one or more electrical currents, therapies, and/or signals can be provided from the power source to the jaw assembly, and/or to one or more features of the jaw assembly such as the one or more jaws, jaw bodies, sealing plates, electrodes, cutting elements, or a combination thereof, via one or more connections, such as wires, cables, plugs, and/or ports. The power source may be any suitable power source. The power source may be a generator. The power source may be of the type described in U.S. Pat. No. 7,282,048B2 issued Oct. 16, 2007, the teachings of which are hereby incorporated by reference herein for all purposes.

The one or more electrical currents, therapies, and/or signals provided by the power source may include monopolar energy, bipolar energy blended energy, or a combination thereof. The one or more electrical currents, therapies, and/or signals may include a cut, waveform, a coagulation waveform, and or a blended waveform. During use, an electrical circuit may be completed by passing monopolar energy from the power source to the jaw assembly and/or one or more features of the jaw assembly, to the object or anatomical feature of interest, and to a remote pad or electrode. During use, an electrical circuit may be completed by passing bipolar energy from the power source to an active electrode or active feature of the jaw assembly, through the object or anatomical feature of interest, and to a return electrode or portion of the jaw assembly. During use, the cut waveform may be delivered continuously from the power source to the medical device, the jaw assembly, and/or one or more features of the jaw assembly, and can be described as a higher current/lower voltage waveform compared to the coagulation waveform. During use, the coagulation waveform may be modulated or interrupted from the power source to the medical device, the jaw assembly, and/or one or more feature of the jaw assembly, and can be described as a lower current/higher voltage waveform compared to the cut waveform. During use, the blended waveform may be a combination of a cut waveform and a coagulation waveform. The blended waveform may advantageously allow a user to coagulate an object or anatomical feature while also cutting the object or anatomical feature. The blended waveform may be of the type described in the above-mentioned U.S. Pat. No. 7,282,048B2 issued Oct. 16, 2007.

The medical device may include a hand piece. The hand piece may function to house, support, and/or contain the introducer, the jaw assembly, and/or one or more features of the jaw assembly, such as the one or more jaws, jaw bodies, sealing plates, electrodes, cutting elements, or a combination thereof. The hand piece may function to house, support, and/or contain the parts of components and/or mechanism required for moving the jaw assembly, the one or more jaws, jaw bodies, sealing plates, cutting elements, or a combination thereof. The hand piece may include sufficient user controls for operating, actuating, moving, reciprocating, and/or manipulating the jaw assembly, the one or more jaws, jaw bodies, sealing plates, cutting elements, or a combination thereof. The user controls may be located anywhere on medical device, the hand piece, at a remote location, or a combination thereof. The one or more user controls may include one or more triggers, wheels, levers, buttons, knobs, the like, or a combination thereof. The hand piece may function to be held and or manipulated with one hand or with both hands of an operator, surgeon, and/or one or more assistants.

The medical device may include one or more mechanisms. The one or more mechanisms may function to manipulate, actuate, reciprocate, or otherwise move or operate the jaw assembly, the one or more jaws, jaw bodies, sealing plates, electrodes, cutting elements, or a combination thereof. For example, the one or more mechanisms may function to move, rotate, reciprocate, actuate, extend, retract, open, and/or close the jaw assembly, the one or more jaws, jaw bodies, sealing plates, electrodes, cutting elements, or a combination thereof. The one or more mechanisms may function to move the jaw assembly, and/or one or more of the jaws, between a closed or gripping position and an open position. The mechanisms may comprise any suitable mechanisms, members, features, biasing members, fasteners, and/or assemblies for moving, rotating, reciprocating, actuating, opening, and/or closing the jaw assembly, the one or more jaws, jaw bodies, sealing plates, cutting elements, or a combination thereof.

The jaw assembly or the one or more jaws may move or pivot when moving between a closed or gripping position and an open position. In the closed position, the jaw assembly or the one or more jaws may cooperate to effect an object or anatomic feature. That is, an object or anatomical feature may be placed within the jaw assembly, between the jaws, between sealing or gripping surfaces, or a combination and then be effected. The object or anatomical feature can be effected by moving the jaw assembly into the closed position. In the closed position, the jaw assembly or the one or more jaws may touch or be in close proximity to one another. In the closed position, the jaw assembly or the one or more jaws may exert a gripping force on the object or anatomical feature that is greater than a gripping force exerted on the object or anatomical feature when the jaw assembly is in an open position. In the closed position, the object or anatomical feature may be subjected to or exposed to a suitable electrical current, therapy, anchor signal. In the closed or gripping position, the cutting element can be moved to effect the object or anatomical feature located in the jaw assembly. In the closed position, the medical device or the jaw assembly can be moved or swept across an object or anatomical feature to effect the object or anatomical feature with one or more edges. In the closed position, one or more currents, signals, and/or therapies can be provided to the jaw assembly and/or to features of the jaw assembly. Using the hand piece, the introducer, or a mechanism in the hand piece as a reference, when moving the jaw assembly or the one or more jaws into the closed or gripping position, the first body may move or pivot towards the second body; the second body may move or pivot towards the first body; both bodies may move or pivot towards one another; or a combination thereof.

In the open position, the jaw assembly or the one or more jaws may be in a spaced apart relationship relative to one another. In the open position, the jaw assembly or the one or more jaws may cooperate to effect an object or anatomic feature. In the open position, the jaw assembly or the one or more jaws may exert a gripping force on the object or anatomical feature that is less than a gripping force exerted on the object or anatomical feature when the jaw assembly is in the closed position. In the open position, the object or anatomical feature may be subjected to or exposed to a suitable electrical current, therapy, and/or signal. In the open position, the cutting element can be moved to effect the object or anatomical feature located in the jaw assembly. In the open position, the medical device or the jaw assembly can be moved or swept across an object or anatomical feature to effect the object or anatomical feature with one or more edges. In the open position, one or more currents, signals, and/or therapies can be provided to the jaw assembly and/or to features of the jaw assembly. Using the hand piece, the introducer, or a mechanism in the hand piece as a reference, when moving the jaw assembly or the one or more jaws into the open position, the first body may move or pivot away from the second body; the second body may move or pivot away from the first body; both bodies may move or pivot away from one another; or a combination thereof.

The medical device may include one or more introducers. The introducer may function to permit a portion of the medical device to be inserted into a patient or the anatomy, while a portion of the medical device remains outside of the patient or anatomy. The jaw assembly or the one or more features of the jaw assembly may be fixedly connected to the introducer. The jaw assembly or the one or more features of the jaw assembly may move within the introducer between an extended position and a retracted position. In the extended position, the jaw assembly and/or the one or more features of the jaw assembly may extend or project from the distal end of the introducer. In the retracted position, at least a portion the jaw assembly and/or the one or more features of the jaw assembly may retract or move proximally relative to the hand piece into a hollow or inner portion of the introducer. The introducer may be an elongated, tubular member that extends along a longitudinal axis between opposing proximal and distal ends. The proximal end of the introducer may be connected to the hand piece. The distal end may be inserted into a patient or the anatomy. The introducer may be substantially straight; may include one or more angles, bends or arcs; or a combination thereof. The introducer may be substantially rigid; substantially flexible; substantially resilient; or a combination thereof.

The medical device may include one or more jaw assemblies. The jaw assembly may be configured to surgically effect an object or anatomical feature. For example, the jaw assembly may be used to capture, grip, grasp, and/or manipulate an object or anatomical feature; provide a clamping force to secure an object or anatomical feature; provide retraction of an object or anatomical feature; provide a compression or gripping force across an object or anatomical feature; or a combination thereof. The jaw assembly may be used in electrosurgery to cut, coagulate, cauterize, dissect, and/or fulgurate an object or anatomical feature. The jaw assembly may be moved, pivoted, or flexed between an open and a closed or gripping position, as was described above.

The medical device and/or the jaw assembly may include one or more jaws. The jaws may be configured to surgically effect an object or anatomical feature. For example, the jaws may be used to rapture, grip, grasp, and/or manipulate an object or anatomical feature; provide a clamping force to secure an object or anatomical feature; provide retraction of an object or anatomical feature; provide a compression or gripping force across an object or anatomical feature; or a combination thereof. The jaws may be used in electrosurgery to cut, coagulate, cauterize, dissect, and/or fulgurate an object or anatomical feature (e.g., surgically effect an object or anatomical feature). The jaws may be moved, pivoted, or flexed between an open and closed position, described above. The one or more jaws may include or be referred to herein as an upper jaw, a lower jaw, a first jaw, a second jaw, or a combination thereof. Each of the one or more jaws may carry, or may be comprised of, one or more jaw bodies, sealing plates, cutting elements, electrodes, insulators, or a combination thereof.

The jaw bodies may be configured to surgically effect an object or anatomical feature. For example, the jaw bodies may be used to capture, grip, grasp, and/or manipulate an object or anatomical feature; provide a clamping force to secure an object or anatomical feature; provide retraction of an object or anatomical feature; provide a compression or gripping force across an object or anatomical feature; or a combination thereof. The jaw bodies may be used in electrosurgery to cut, coagulate, cauterize, dissect, and/or fulgurate an object or anatomical feature. The jaw bodies may be moved, pivoted, or flexed between art open and closed position, described above. The jaw bodies may include, or may be referred to herein as, an upper jaw body, a lower jaw body, a first jaw body, a second, jaw body, or a combination thereof.

The jaw bodies may have any suitable shape or cross section. For example, the jaw bodies may be generally straight, curved, or both. The jaw bodies may be rectangular, ovoid, elongated, or a combination thereof. Each of the jaw bodies may be substantially rigid, flexible, resilient, or a combination thereof. Each of the jaw bodies may have generally the same shape, mass, and/or size, or the shape, mass, and/or size of each jaw body may be different. For example, a first or upper jaw body may be larger, smaller, or be the same size as a second or lower jaw body. For example, a first or upper jaw body may have a larger, smaller, or the same mass as a second or lower jaw body. One or more of the jaw bodies may generally have the same mass, size, and/or shape as one or more of the sealing plates. Alternatively, or the mass, size, and/or shape of one or more of the jaw bodies may be different than the mass, size, and/or shape of the one or more sealing plates.

The medical device, the jaw assembly, and/or the one or more jaws may include one or more sealing plates. The sealing plate may be configured to effect an object or anatomical feature. For example, the sealing plate may be used to capture, grip, grasp, and/or manipulate an object or anatomical feature; provide a clamping force to secure an object or anatomical feature; provide retraction of an object or anatomical feature; provide a compression or gripping force across an object or anatomical feature; or a combination thereof. The sealing plate may be used in electrosurgery to cut, coagulate, cauterize, dissect, and/or fulgurate an object or anatomical feature. The sealing plate may be carried on the first jaw, the first jaw body, on the second jaw, on the second jaw body, or a combination thereof. The sealing plate may be an electrode in electrical communication with the power source. A profile of one of the sealing plates may be larger, smaller, or may fit within a profile of another sealing plate, jaw body, or both.

The one or more sealing plates can moveable or reconfigurable so that the profile, edge, or periphery of a seating plate matches or corresponds to a profile, edge, or periphery of another sealing plate, jaw body, or both. The one or more sealing plates can moveable or reconfigurable so that the profile, edge, or periphery of a sealing plate extends or projects beyond a profile, edge, or periphery another sealing plate, jaw body, or both. For example, an edge, profile, or periphery of a sealing plate can be moved or made to project beyond a distal end of the jaw assembly so that the sealing place can function as a bipolar or a monopolar cutting element. The sealing plate may define one or more arms. The one or more arms may be individually or together electrically connected to the power source. The one or more arms may have a common polarity, or the polarities may be opposite. The one or more arms may have a floating polarity. The one or more arms may be together in electrical communication or may be electrically isolated from one another. The one or more arms may be moveable relative to one another, another electrode or sealing plate, one or both of the jaw bodies, or a combination thereof.

The one or more sealing plates may be fabricated from a suitable material such as sheet metal. The sealing plates may have a constant thickness or the thickness may vary between a proximal and distal end thereof. The thickness of the sealing plate may be on the order of approximately 0.02 mm or more, 0.04 mm or more, 0.05 mm or more, 0.10 mm or more, 0.20 mm or more, 0.30 mm or more, 0.40 mm or more, 0.50 mm or more, 0.60 mm or more, 0.70 mm or more, 0.75 mm or more. The thickness of the sealing plate may be on the order of approximately 1.00 mm or less, 0.90 mm or less, 0.80 mm or less, 0.75 mm or less. Preferably, the thickness of the sealing plate is between about 0.05 mm and approximately 0.75 mm.

One of the jaw bodies, electrodes, and/or sealing plates may be constructed from a bulk conductive material. One or more of the jaw bodies and/or sealing plates may be an electrode or in communication with an electrode. One of the jaw bodies, electrodes, and/or sealing plates may be constructed at least partially from a first conductive, material and the other jaw body and/or sealing plate may be constructed from a second conductive material. The first and second conductive materials may be the same materials or may be different. For example, the first conductive material may have a thermal conductivity that is generally the same as, greater than, or less than the thermal conductivity of the second conductive material. For example, the first conductive material may have a specific heat that is generally the same as, greater than, or less than the specific heat of the second conductive material.

One or more of the sealing plates may have a mass that is less than the mass of one or more of the jaw bodies so that the one or more sealing plates heat more than the one or more jaw bodies with more mass. Accordingly, during use and when connected to the power source, the one or more sealing plates with less mass may become the active electrode rather than a return electrode. One or mare of the sealing plates may have a specific heat that is less than the specific heat of one of more of the jaw bodies so that the one or more jaw bodies heat less than the one or more sealing plates. Accordingly, the one or more sealing plates with less specific heat may become the active electrode rather than a return electrode. One or more of the sealing plates may have a thermal conductivity that is less than the thermal conductivity of one of more of the jaw bodies so that the one or more jaw bodies heat less than the one or more sealing plates. Accordingly, the one or more sealing plates with less thermal conductivity may become the active electrode rather than a return electrode.

One or more of the jaw bodies, sealing plates, or both may be at least partially constructed from a conductive material and at least partially constructed from or covered by an insulator. For example, one or more of the jaw bodies, sealing plates, or both may have an outer or upper surface and/or side surfaces that are at least partially constructed from or covered by an insulator. As used herein, the outer or upper surface may oppose a gripping or sealing surface and the side surface may be generally perpendicular to the outer or upper surface.

The one or more jaw bodies, sealing plates, electrodes, cutting elements, or a combination thereof may be electrically connected to the power source. One or more jaw bodies, sealing plates, electrodes, cutting elements, or a combination thereof may be electrically connected to the power source via one or more wires, connections, and/or plugs. One or more jaw bodies, sealing plates, electrodes, or a combination thereof may have a first polarity (e.g. '−'). One or more jaw bodies, sealing plates, electrodes, or a combination thereof may have a second polarity (e.g. '+'). One or more jaw bodies, sealing plates, electrodes, or a combination thereof may have a floating polarity. A floating polarity may mean that the jaw body, sealing plate, or electrode is disconnected or is not connected to the power source. Instead, the jaw body, sealing plate, or electrode may selectively contact another jaw body, sealing plate, or electrode connected to the power source so that the jaw body, sealing plate, or electrode with the floating polarity takes on the same polarity as the jaw body, sealing plate, or electrode that it contacts. One or more jaw bodies, sealing plates, or both may be electrically disconnected from the power source.

An object or anatomical feature can be surgically effected by placing the object or anatomical feature between or in contact with the jaw assembly, the jaw bodies, sealing plates, edges of the jaw body, edges of the sealing plate, electrodes, or a combination thereof while passing a suitable current or therapy signal to the jaw assembly. The object or anatomical feature can be effected by moving or sweeping at least a portion of the jaw assembly, the one or more jaw bodies, electrodes, and/or sealing plates across an object or, anatomical feature so that a portion (e.g. one or more edges) of one or more of the jaw bodies, electrodes and/or sealing plates contacts the of or anatomical feature while a suitable current or therapy signal is provided to the jaw assembly.

The one or more jaw bodies, electrodes, and/or sealing plates may include one or more edges. The one or more edges may be defined as being generally perpendicular to an outer or top surface of the jaw body; generally perpendicular to an outer or lower surface of the jaw body; generally perpendicular to a gripping or sealing surface of the jaw body, sealing plate or both; or a combination thereof. The one or more edges may be located at a distal end or nose portion of a jaw body, sealing plate, electrodes, or a combination thereof; at one or more lateral portions of a jaw body, sealing plate, electrodes, or a combination thereof.

One or more edges of the one or more jaw bodies, electrodes, and or sealing plates may extend or protrude beyond a profile; or one or more edges of another of the one or more other jaw bodies, one or more other sealing plates, or a combination thereof. One or more edges of the one or more jaw bodies, electrodes, and/or sealing plates may under hang or be located within a profile or within one or more edges of another of the one or more jaw bodies, one or more sealing plates, or a combination thereof one or more edges of the one or more jaw bodies, electrodes, and/or sealing plates may be generally flush with one or more edges of another of the one or more jaw bodies, one or more sealing plates, or a combination thereof.

The one or more jaws, jaw bodies, electrodes, sealing plates, or a combination thereof may include a sealing surface. The sealing surface may function as a gripping surface. The sealing surface may function to effect, capture, grip, grasp, and/or manipulate an object or anatomical feature; provide a clamping force to secure an object or anatomical feature; provide retraction of an object or anatomical feature; provide a compression or gripping force across an object or anatomical feature; or a combination thereof. The sealing surface may be at least partially conductive. The sealing surface may be used in electrosurgery to effect, cut, coagulate, cauterize, dissect, and/or fulgurate, an object or anatomical feature. The sealing surface may be at least partially smooth, flat, contoured, serrated, textured, toothed, undulating, wave-shaped, planar, irregular, knurled, grit blasted, or a combination thereof. The sealing surface may include one or more surfaces that are horizontal, vertical, canted, or a combination thereof relative to a longitudinal axis of the introducer. The sealing surface may include one or more ridges, teeth, mouse teeth, gaps, openings, of a combination thereof.

The one or more jaws, jaw bodies, sealing plates, electrodes, sealing surfaces, or a combination thereof may include one or more insulators. The insulators referred to herein may be an insulator, an insulating spacer, or both. The insulators may function to insulate, restrict, and/or prevent electricity, current, and/or therapy signals from passing between features of the jaw assembly, the medical device, or a combination thereof. The insulator may function to provide a stand off or spacing between the jaw bodies, sealing plates, electrodes, sealing surfaces, or a combination thereof when the jaw assembly is in a closed or gripping position. The insulator may restrict or prevent electricity, current, and/or therapy signals from passing between a jaw body and another jaw body; between a sealing plate and another sealing plate; between a jaw body and a sealing plate; between a cutting element, jaw body, and/or sealing plate; or any combination thereof. The insulator may function to prevent the jaw assembly, the one or more jaw bodies, and/or sealing plates or surfaces from arcing during electrosurgery. The insulator may be located in a groove or channel to insulate a cutting element from a jaw body, sealing plate, or both. The insulator may be one or more insulators located between a jaw body and a sealing plate. The insulator may be located between a jaw body and a sealing plate. The insulator may be located above or below one or more of the jaw bodies, sealing plates, or both. The insulator may over hang, under hang, or fit within a profile of one or more of the sealing plates, jaw bodies, or a combination thereof. The insulator may be one or more projections or nubs projecting from the gripping surface of the sealing plate, jaw body, or both. The insulator may be formed from any suitable material having insulating properties. For example, the insulator may be constructed from Nylon, PEEK, silicon rubber, a ceramic material, or a combination thereof.

The one or more jaws, jaw bodies, sealing plates, sealing surfaces electrodes, or a combination thereof may include one or more cutting elements. The cutting element may function to effect an object or anatomical feature. For example, the cutting element may be configured to cut or dissect an object or anatomical feature. The cutting element may effect the object of anatomical feature while the jaw assembly is in an open or closed position. The cutting element may be located in a cutting recess. The cutting element may be moved, reciprocated, and/or rotated within the jaw assembly when the jaw assembly is in an open and/or closed position. The cutting element may be moved so that cutting element extends or projects beyond a distal end of the jaw assembly, either of the sides of the jaw assembly, or a combination thereof. The one or more cutting elements may be electrically connected to a source of current or, power so that the cutting element can be used in electrosurgery. The cutting element may be an electrode. The electrode may be integrally formed with one or more of the jaw bodies.

FIG. 1 illustrates a jaw assembly 100. The jaw assembly 100 includes a first jaw 102 and a second jaw 104. The first jaw 102 includes a first jaw body 106. The first body 106 may be constructed from a bulk conductive material. The second jaw 104 includes a second jaw body 108 and a sealing plate 110. The second jaw body 108 may be constructed from a non-conductive material; may be electrically disconnected from either or both of the first jaw body 106 and the sealing plate 110; may be non-participating in the bipolar circuit; may be temporarily or permanently disconnected from the power source 210 (FIG. 11); or a combination thereof. An edge or periphery 118 of the sealing plate 110 extends beyond an edge or periphery 119 of the first jaw body 106, the second jaw body 108, or both. The sealing plate 110 includes a sealing surface 112. The sealing plate 110 and/or the sealing surface 112 may optionally include one or more insulators 114. The sealing plate and/or the sealing surface 112 may optionally include a cutting element 116 located within a cutting recess 117.

With continued reference to FIG. 1, the first jaw body 106 has a first polarity (e.g. '−') and the sealing plate 110 has an opposing polarity (e.g. '+') or vice versa. That is, the first jaw body 106 is electrically connected to first pole of a power source 210 (FIG. 13) and the sealing plate 110 is electrically connected to a second pole of the power source 210, or vice versa. The sealing plate 110 is smaller than the first jaw body 106 so that in a bipolar circuit, the sealing plate 110 acts as the active electrode and the first jaw body 106 acts as the return electrode.

With continued reference to FIG. 1, in a first use state, an object or anatomical feature can be surgically effected by placing the anatomical feature between the first jaw body 106 and the sealing plate 110 and passing a suitable therapy current between the sealing plate 110 and the first jaw body 106.

With continued reference to FIG. 1, in a second use state, an object or anatomical feature can be surgically effected by moving or sweeping the jaw assembly 100 across the object or anatomical feature. In this regard, the edge 118 of the sealing plate 110 can contact the object or anatomical feature while a suitable therapy current is passed between the sealing plate 110 and the first jaw body 106.

With continued reference to FIG. 1, in a third use state, an object or anatomical feature can be surgically effected by placing the anatomical feature between the first jaw body 106 and the sealing plate 110 and moving the cutting element 116 through the anatomical feature.

With continued reference to FIG. 1, the medical device 100 does not require any pole switching (i.e., the medical device is free of pole switching) when the medical device 100 is used in the first, second, or third states.

Figure 2:
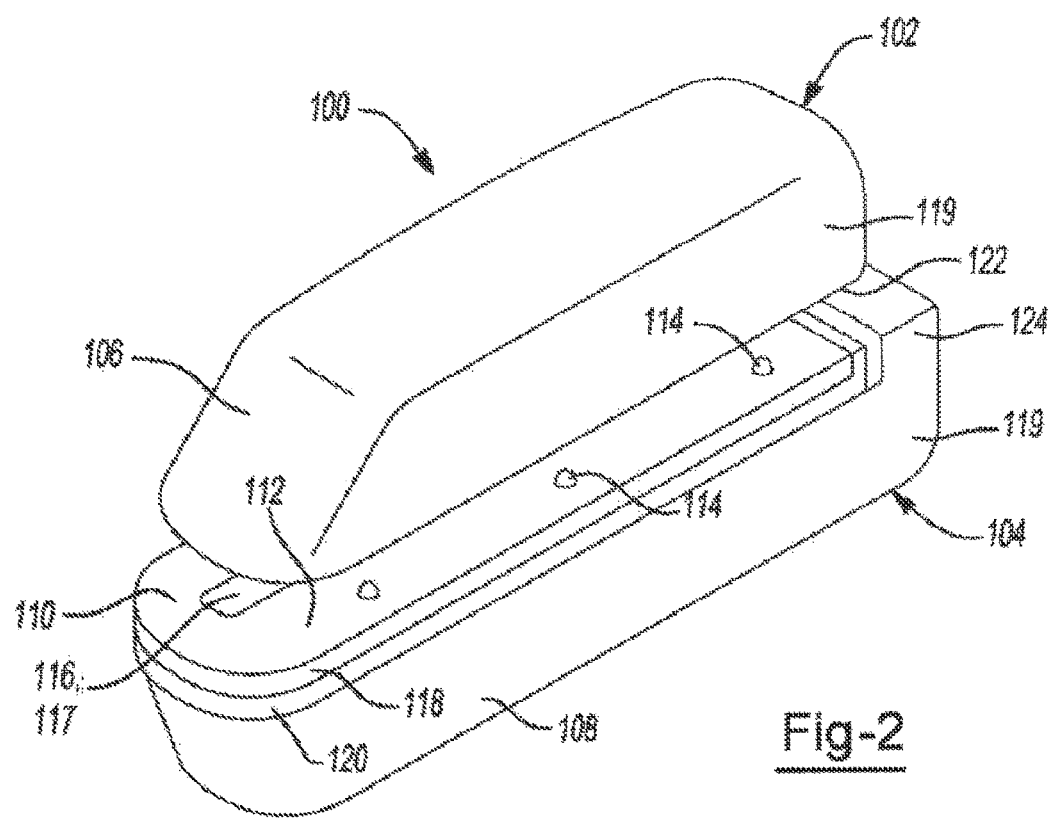
FIG. 2 is a perspective view of a jaw assembly.

FIG. 2 illustrates a jaw assembly 100. The jaw assembly 100 includes a first jaw 102 and a second jaw 104. The first jaw 102 includes a first jaw body 106. The first jaw body 106 may be constructed from a bulk conductive material. The second jaw 104 includes a second jaw body 108. The second jaw body 108 may be constructed from a bulk conductive material. The second jaw 104 includes a sealing plate 110 and an insulator 120 located between the second jaw body 108 and the sealing plate 110. An edge or periphery 118 of the sealing plate 110 extends beyond an edge or periphery 119 of the first jaw body 106, the second jaw body 108, or both. The sealing plate 110 includes a sealing surface 112. The sealing plate 110 may optionally include one or more insulators 114. The sealing plate 110 may optionally include a cutting element 116 located within a cutting recess 117.

With continued reference to FIG. 2, the first jaw body 106 has a first polarity e.g. '−') and the sealing plate 110 has a second polarity (e.g. '+'), or vice versa. That is, the first jaw body 106 is electrically connected to first pole of a power source 210 (FIG. 13) and the sealing plate 110 is electrically connected to a second pole of the power source 210 (FIG. 13), or vice versa. The second jaw body 108 has a floating polarity (e.g. 'o').

In another form, with continued reference to FIG. 2, the second jaw body 108 has a first polarity (e.g. and the sealing plate 110 has a second polarity (e.g. '+'), or vice versa. That is, in this form, the second jaw body 108 is electrically connected to a first pole of the power source 210 and the sealing plate 110 is electrically connected to a second pole of the power source 210, or vice versa. In this form, the first jaw body 106 has a floating polarity (e.g. 'o'). In other words, in this form, the first jaw body 106 is not initially connected to a particular pole of the power source 210.

With continued reference to FIG. 2, the sealing plate 110 is smaller in size and/or mass than the first jaw body 106 and/or smaller than both the first and second jaw bodies 106, 108. Accordingly, during use, and/or when connected to the power source 210, the sealing plate 110 acts as the active electrode and the first jaw body 106 and/or both the first and second jaw bodies 106, 108 act as the return electrode.

With continued reference to FIG. 2, when the jaw assembly 100 is in the open position, the first jaw body 106 and the second jaw body 108 are not in electrical communication with one another. However, when the jaw assembly 100 is in the closed position, at least a proximal portion 122 of the first jaw body 106 and at least a proximal portion 124 of the second jaw body 108 are in contact. Thus, in the closed position, the first jaw body 106 and the second jaw body 108 are in electrical communication and have the same polarity or share a common polarity. Thus, in the closed position, the first and the second jaw bodes 106, 108 have a polarity that is opposite the polarity of the sealing plate 110.

With continued reference to FIG. 2, in a first use state, an object or anatomical feature can be surgically effected by placing the object or anatomical feature between the first jaw body 106 and the sealing plate 110 and passing a suitable therapy current between the sealing plate 110 and the first jaw body 106 or between the sealing plate 110 and the second jaw body 108.

With continued reference to FIG. 2, in a second use state, an object or anatomical feature can be surgically effected by moving or sweeping the jaw assembly 100 across the object or anatomical feature so that the edge 118 of the sealing plate 110 contacts the object or anatomical feature while a suitable therapy current is passed between the sealing plate 110 and either or both of the first jaw body 106 and the second jaw body 108. The jaw assembly 100 may be in the open position or the closed position in this second use state.

With continued reference to FIG. 2, in a third use state, an object or anatomical feature can be surgically effected by placing the anatomical feature between, the first jaw body 106 and the sealing plate 110 and moving the cutting element 116 through the anatomical feature.

Figure 3:
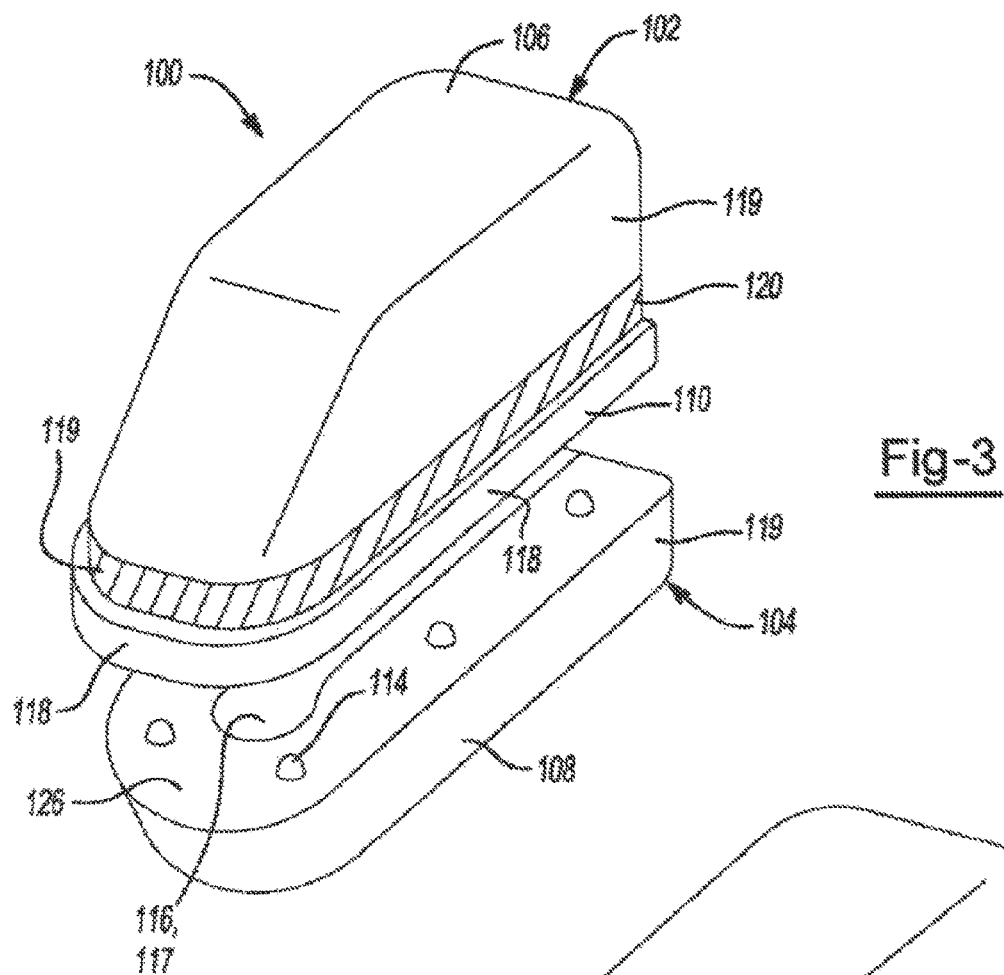
FIG. 3 is a perspective view of a jaw assembly.

FIG. 3 illustrates a jaw assembly 100. The jaw assembly 100 includes a first jaw 102 and a second jaw 104. The first jaw 102 includes a first jaw body 106, a sealing plate 110, and an insulator 120 located therebetween. An edge or periphery 118 the sealing plate 110 overhangs or extends beyond of an edge or periphery 119 of the insulator 120, the first jaw body 106, and/or the second jaw body 108. The second jaw 104 includes a second jaw body 108. One or both of the first jaw body 106 and the second law body 108 may be constructed from a bulk conductive material. The second jaw body 108 includes a sealing surface 126. The sealing surface 126 may optionally include one or more insulators 114. The sealing surface may optionally includes a cutting element 116 located within a cutting recess 117.

With continued reference to FIG. 3, the sealing plate 110 is smaller than the first jaw body 106 or is smaller than both the first and second jaw bodies 106, 108 combined. Thus, during use, when connected to the power source 210 (FIG. 13), the sealing plate 110 acts as the active electrode and the first jaw body 106 or both the first and second jaw bodies 106, 108 act as the return electrode.

With continued reference to FIG. 3, in a first electrosurgical form, the first jaw body 106 and the second jaw body 108 have a first polarity (e.g. '−') and the sealing plate 110 has a second polarity (e.g. '+'), or vice versa. That is, the first jaw body 106 and the second jaw body 108 are individually or together electrically connected to first pole of a power source 210 and the sealing plate 110 is electrically connected to a second pole of the power source 210, or vice versa.

With continued reference to FIG. 3, in a second electrosurgical form, the first yaw body 106 has a first polarity (e.g. the sealing plate 110 has a second polarity (e.g. '+'), or vice versa, and the second jaw body 104 supports a blended first and second polarity (e.g. '+/−'). That is, the first jaw body 106 is electrically connected to first pole of a power source 210, the sealing plate 110 is electrically connected to a second pole of the power source 210 and the second jaw body 108 is electrically connected to a blended first and second pole of the power source 210.

With continued reference to FIG. 3, in a first use state, an object or anatomical feature can be surgically effected by placing the object or anatomical feature between the sealing plate 110 and the second jaw body 108 and passing a suitable therapy current between the sealing plate 110 and the second jaw body 108.

With continued reference to FIG. 3, in a second use state, an object or anatomical feature cane surgically effected by moving or sweeping the jaw assembly 100 across the object or anatomical feature so that the edge or periphery 118 of the sealing plate 110 contacts the object or anatomical feature while a suitable therapy current is passed between the sealing plate 110 and one or both of the jaw bodies 106, 108.

With continued reference to FIG. 3, in a third use state, an anatomical feature can be surgically effected by placing the anatomical feature between sealing plate 110 and the second jaw body 108 and by passing a suitable therapy between the sealing plate 110 and the second jaw body 108.

Figure 4:
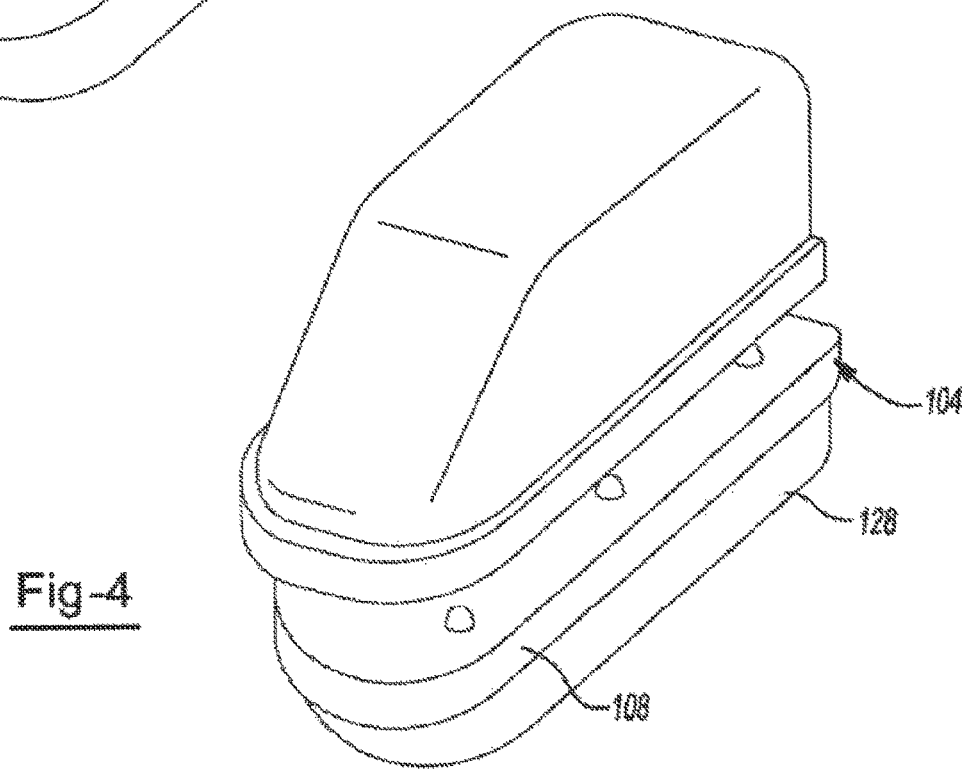
FIG. 4 is a perspective view of a jaw assembly.

FIG. 4 is substantially similar to the FIG. 3 with the addition that the second jaw 104 includes an insulator 128 located below the second jaw body 108.

Figure 5:
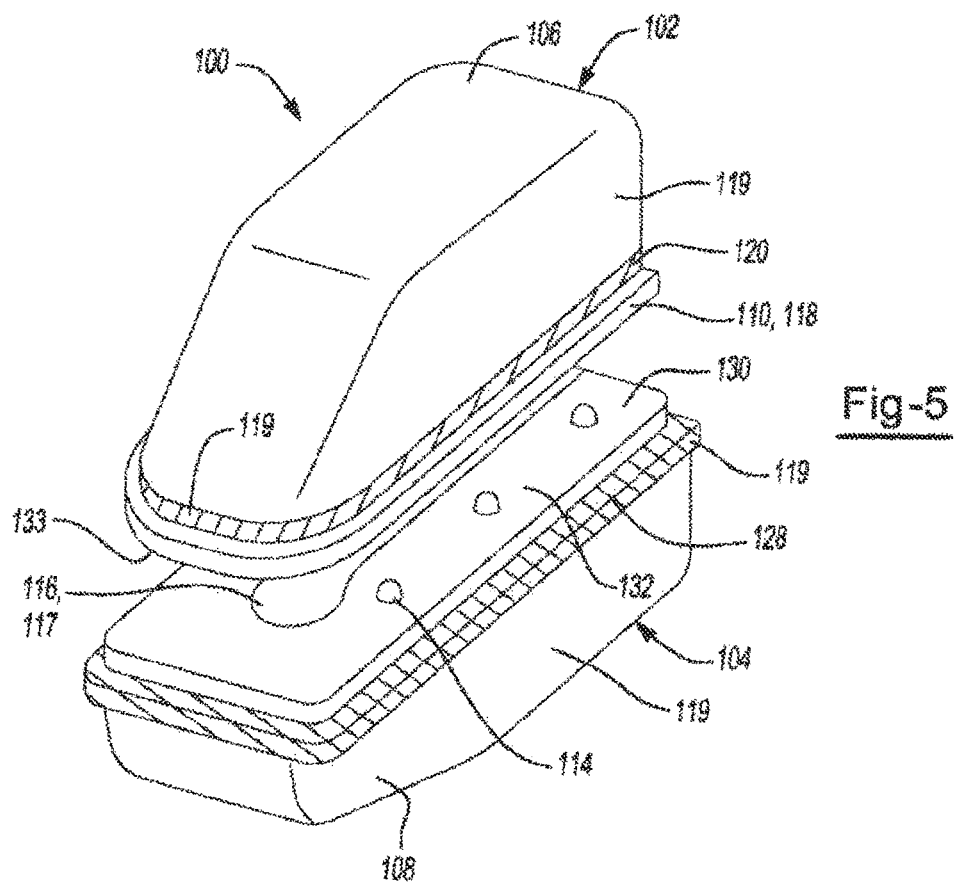
FIG. 5 is a perspective view of a jaw assembly.

FIG. 5 illustrates a jaw assembly 100. The jaw assembly 100 includes a first jaw 102 and a second jaw 104. The first jaw 102 includes a first jaw body 106, a sealing plate 110, and an insulator 120 located therebetween. An edge or periphery 118 of the sealing plate 110 overhangs or extends beyond of an edge or periphery 119 of the insulator 120, the first jaw body 106, and/or a second jaw body 108 of the second jaw 104. The second jaw 104 also includes a sealing plate 130 and an insulator 128 extending between the second jaw body 108 and the sealing plate 130. The sealing plate 130 includes a sealing surface 132 that opposes a sealing surface 133 of the sealing plate 110. One or both of the sealing surfaces 132, 133 may optionally include one or more insulators 114. One or both of the sealing surfaces 132, 133 may optionally include a cutting element 116 located within a cutting recess 117.

With continued reference to FIG. 5, the sealing plate 130 is the same size or smaller than the sealing plate 110, the second jaw body 108, or both so that a profile of the sealing plate 130 fits within a profile of sealing plate 110 and/or the second jaw body 108. The insulator 128 is preferably smaller than the second jaw body 108 so that the insulator 128 under hangs or is located within the profile of the second jaw body 108.

With continued reference to FIG. 5, the first jaw body 106, the second jaw body 108, and the sealing plate 130 have a first polarity (e.g. and the sealing plate 110 has a second polarity (e.g. '+'), or vice versa. That is, the first jaw body 106, the second jaw body 110, and the sealing plate 130 are individually or together electrically connected to a first pole of a power source 210 (FIG. 13) and the sealing plate 110 is electrically connected to a second pole of the power source 210.

With continued reference to FIG. 5, the polarity of the sealing plate 110 can be changed. In other words, in the second use state described below, for example, the sealing plate 110 can have the same polarity as the sealing plate 130.

With continued reference to FIG. 5, the first jaw body 106 or the second jaw body 108 may support a blended polarity (e.g. '+').

With continued reference to FIG. 5, the sealing plate 110 is smaller than the first jaw body 106 and/or the first and second jaw bodies 106, 108. Therefore, during use, when connected to the power source 210, the sealing plate 110 acts as the active electrode and the first jaw body 106 or the first and the second jaw bodies 106, 108 act as the return electrode.

With continued reference to FIG. 5, the sealing plate 110 can moveable or reconfigurable so that the profile or position of the sealing plate 110 matches or corresponds to a profile or position of the second sealing plate 130, or extends or projects beyond a profile or position of the second sealing plate 130. Stated another way, an edge 118 or portion of the sealing plate 110 or 130 can be moved or made to project beyond an end of the jaw assembly 100 (e.g., a distal end, for example) and function as a bipolar or a monopolar cutting blade.

With continued reference to FIG. 5, in a first use state, an object or anatomical feature can be surgically effected by placing the object or anatomical feature between the sealing plates 110, 130 and passing a suitable therapy current between the sealing plates 110, 130.

With continued reference to FIG. 5, in a second use state, an object or anatomical feature can be surgically effected by moving or sweeping the jaw assembly 100 across the anatomical feature so that the edge 118 of the sealing plate 110 contacts the object or anatomical feature while a suitable therapy current is passed between the sealing plate 110 and one or both of the jaw bodies 106, 108.

With continued reference to FIG. 5, in a third use state, an of or anatomical feature can be surgically effected by placing the object or anatomical feature between the sealing plates 110, 130 and moving the cutting element 116 through the anatomical feature.

Figure 6:
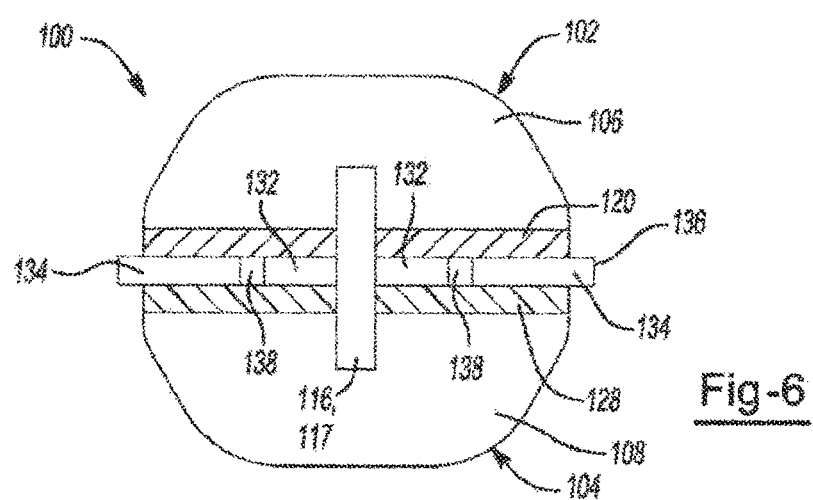
FIG. 6 is a cross-sectional view of a jaw assembly.

FIG. 6 illustrates a cross section of a jaw assembly 100. The jaw assembly 100 includes a first jaw 102 and a second jaw 104. The first jaw 102 includes a first jaw body 106 and a first insulator 120. The second jaw 104 includes a second jaw body 108 and a second insulator 128.

With continued reference to FIG. 6, one of the jaw bodies 106, 108 includes first sealing plates or medial electrodes 132, and the other of the jaw bodies 106, 108 includes laterally located second sealing plates or electrodes 134. The second sealing plates 134 have an edge or periphery 136 that overhangs or extends, beyond an edge or periphery of the insulators 120, 128, one or both of the jaw bodies 106, 108, or a combination thereof. In some configurations, the second sealing plates 134 may be moveable so that the edge or periphery 136 can under hang, be flush with, or extend beyond the edge or periphery of the insulators 120, 128, one or both of the jaw bodies 106, 108, or a combination thereof. A gap 138 is defined between the first or medial electrodes 132 and the second sealing plates 134 on respective sides of an optional cutting element 116 located within an optional channel 117 so that the corresponding first and second sealing plates 132, 134 are not in electrical contact in some configurations, the cutting element 116 may be integrally formed with the first or medical electrodes 132.

With continued reference to FIG. 6, in, some configurations, the first sealing plates or medial electrodes 132 can be integrally formed with one of the jaw bodies 106, 108. Accordingly, in these configurations, the insulator between the integrally formed first sealing plates 132 and corresponding jaw body 106, 108 may be omitted.

With continued reference to FIG. 6, in a first electrosurgical form, the Last jaw body 106, the second jaw body 108, and the first sealing plates or medial electrodes 132 have a first polarity (e.g. '−') and the second sealing plates 134 have a second polarity (e.g. '+'), or vice versa. That is, the first jaw body 106, the second jaw body 110, and the first sealing plates or medial electrodes 132 are individually or together electrically connected to the first pole of a power source 210 (FIG. 13) and the second sealing plates 134 are electrically connected to a second pole of the power source 210, or vice versa.

With continued reference to FIG. 6, in a second electrosurgical form, the first jaw body 106 and the second jaw body 108 have a first polarity (e.g. '−') and the first sealing plates 132 or medial electrodes have an opposing polarity (e.g. '+'), or vice versa. That is, the first jaw body 106 and the second jaw body 110 are individually or together electrically connected to one or more first poles of a power source 210, and the first sealing plates 132 or medial electrodes are electrically connected to a second opposing pole of the power source 210, or vice versa. The polarity of the second sealing plates 134 can be changed (e.g., or '+') depending on a particular use state, described below.

With continued reference to FIG. 6, in a first use state, the second sealing plates 134 have a polarity that is opposite the first sealing plates or medial electrodes 132, but the same polarity as the jaw bodies 106, 108 (e.g. '−'), or vice versa. An object or anatomical feature can be surgically effected by placing the object or anatomical feature between the jaw bodies 102, 104 and passing a suitable therapy current between the sealing plates 132 and the sealing plates 134, the jaw bodies 106, 108, or a combination thereof.

With continued reference to FIG. 6, in a second use state, the sealing plates 132, 134 can have the same polarity (e.g., '+'), but a polarity that is opposite the polarity of the jaw bodies 106, 108 (e.g., or vice versa. In a second use state, an object or anatomical feature can be surgically effected by moving or sweeping the jaw assembly 100 across the object or anatomical feature so that the edge 136 of the sealing plates 134 contacts the anatomical feature while a suitable therapy current is passed between the sealing plate 134, or the sealing plates 132, 134 and the jaw bodies 106, 108.

With continued reference to FIG. 6, in a variant of the second use state, the sealing plates or medial electrodes 132 need not have the same polarity as the sealing plates 134. That is, in the variant of the second use state, the sealing plates or medial electrodes 132 may have the same polarity as the jaw bodies 106, 108, or the sealing plates 134 may be free of any polarities. In the variant of the second use state, an object or anatomical feature can be surgically effected by moving or sweeping the jaw assembly 100 across the anatomical feature so that the edge 136 of the sealing plate 134 contacts the anatomical feature while a suitable therapy current is passed between the sealing plate 134 and the jaw bodies 106, 108.

In a third use state, an object or anatomical feature can be surgically effected by placing the anatomical feature between the first jaw bodies 106, 108 and moving the cutting element 116 through the anatomical feature.

Figure 7:
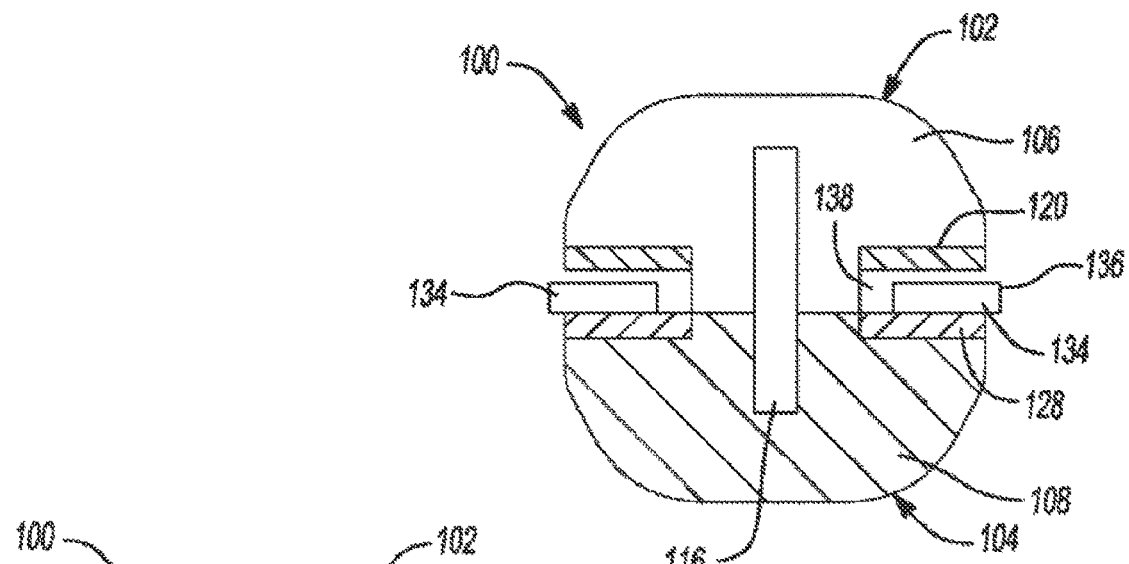
FIG. 7 is a cross-sectional view of a jaw assembly.

FIG. 7 illustrates a cross section of a jaw assembly 100. The jaw assembly 100 includes a first jaw 102 and a second jaw 104. The first jaw 102 includes a first jaw body 106 and an insulator 120. The second jaw 104 includes a second jaw body 108, an insulator 128, and sealing plates 134.

With continued reference to FIG. the sealing plates 134 have an edge or periphery 136 that extends beyond an edge or periphery of the insulators 120, 128, one or both of the jaw bodies 106, 108, or a combination thereof. The sealing plates 134 can be moveable so that the edge or periphery 136 under hangs, is flush with, or extends beyond an edge or periphery of the insulators 120, 128, one or both of the jaw bodies 106, 108, or a combination thereof. Leap 138 is defined between the sealing plates 134 and the jaw body 106. The gap 138 can also be defined between edges of the sealing plates 134 and edges of the first insulator 120. Optionally, the jaw assembly 100 includes a cutting element 116 located within a channel 117.

With continued reference to FIG. 7, the first jaw body 106 and the second jaw body 108 have a first polarity (e.g. '−') and the sealing plates 134 have a second polarity (e.g. '+'), or vice versa. That is, the first jaw body 106 and the second jaw body 110 are individually or together electrically connected to the first pole of a power source 210 (FIG. 13) and the sealing plates 134 are electrically connected to a second pole of the power source 210, or vice versa.

With continued reference to FIG. 7, in a first use state, an object or anatomical feature can be surgically effected by placing the anatomical feature between the jaw bodies 106, 108 and passing a suitable therapy current between the sealing plates 134 and the jaw bodies 106, 108.

With continued reference to FIG. 7, in a second use state an object or anatomical feature can be surgically effected by moving or sweeping the jaw assembly 100 across the anatomical feature so that the edge or periphery 136 of the second sealing plates 134 contacts the object or anatomical feature while a suitable therapy current is passed between the second sealing plates 134 and one or both of the jaw bodies 106, 108.

With continued reference to FIG. 7, in a third use state, a anatomical feature can be surgically effected by placing the anatomical feature between the jaw bodies 106, 108 and moving the cutting element 116 through the anatomical feature.

Figure 8:
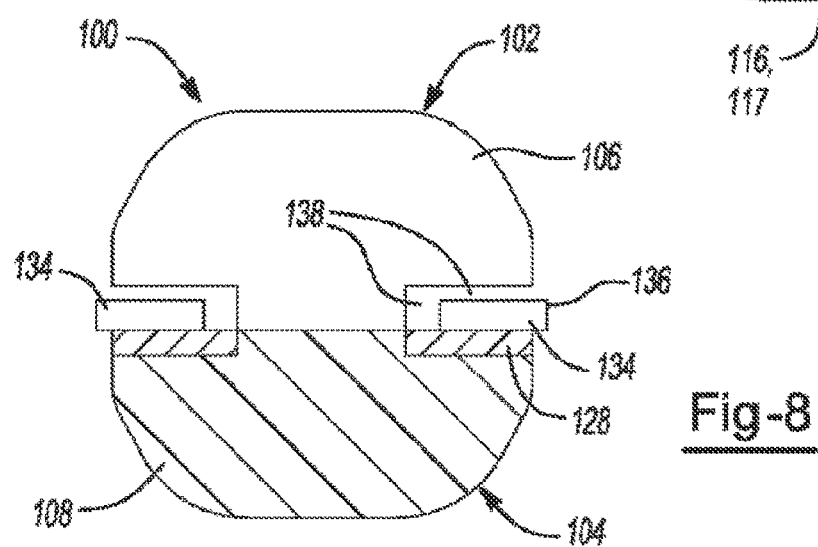
FIG. 8 is a cross-sectional view of a jaw assembly.

FIG. 8 may be substantially similar to FIG. 7. In FIG. 8, however, the first jaw 102 includes a first jaw body 106. The second jaw 104 includes a second jaw body 108, sealing plates 134, and an insulator 128 located between the second jaw body 108 and the sealing plates 134. A gap 138 may be defined between the sealing plates 134 and the first jaw body 106. One or more insulators may be located in the gaps 138 between the first jaw body 106 and sealing plates 134.

Figure 9:
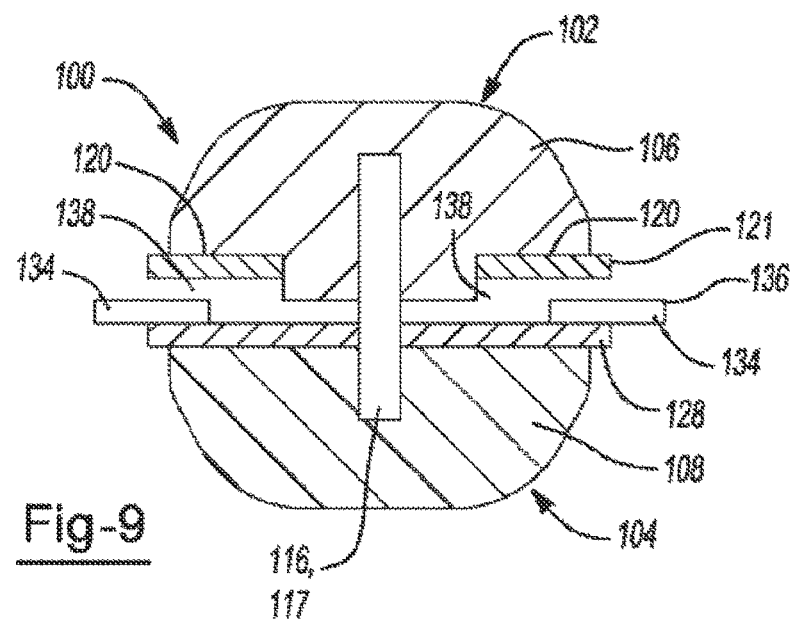
FIG. 9 is a cross-sectional view of a jaw assembly.

FIG. 9 illustrates a cross section of a jaw assembly 100. The jaw assembly 100 includes a first jaw 102 and a second jaw 104. The first jaw 102 includes a first jaw body 106 and a first insulator 120. The second jaw 104 includes a second jaw body 108, a second insulator 128, and sealing plates 134. The insulators 120, 128 have an edge or periphery 121 that extends beyond or overhang an edge or periphery of the jaw bodies 106, 108.

With continued reference to FIG. 9, the sealing plates 134 have an edge or periphery 136 that extend beyond or overhangs an edge or periphery 121 of the insulators 120, 128, an edge or periphery of the one or both of the jaw bodies 106, 108, or a combination thereof. The sealing plates 134 can be moved so that the edge or periphery 136 thereof under hangs, is flush with, or extends beyond the edge or periphery 121 of the insulators 120, 128, the edge or periphery of the one or both of the jaw bodies 106, 108, or a combination thereof. A gap 138 is defined between the sealing plates 134 and the jaw body 106. The gap 138 can also be defined between the sealing plates 134 and the first insulator 120. The jaw assembly 100 also includes a cutting element 116 within a channel 117.

With continued reference to FIG. 9, in a first electrosurgical form, the first jaw body 106 and the second jaw body 108 have a first polarity (e.g. '−') and the sealing plates 134 have a second polarity (e.g. '+'), or vice versa. That is, the first jaw body 106 and the second jaw body 110 are individually or together electrically connected to one or more first poles of a power source 210 (FIG. 13) and the second sealing plates 134 are electrically connected to a second pole of the power source 210, or vice versa.

With continued reference to FIG. 9, in a second electrosurgical form, the first jaw body 106 has a first polarity (e.g. '−') and the sealing plates 134 have a second polarity (e.g. '+'), or vice versa. The second jaw body 108 has a floating polarity (e.g. 'o'); that is, the second jaw body 108 switches to the same polarity as the first jaw body 106 when the jaw assembly 100 is in the closed position and the second jaw body 108 and the first jaw body 106 are in contact.

With continued reference to FIG. 9, in a third electrosurgical form, the first jaw body 106 has a first polarity (e.g. '−') and the second sealing plates 134 have an opposing polarity (e.g. '+'), or vice versa. The second jaw body 108 supports a blended polarity (e.g. '+/−'). That is, the second jaw body 108 is electrically connected to a blended first and second pole of the power source.

Figure 10:
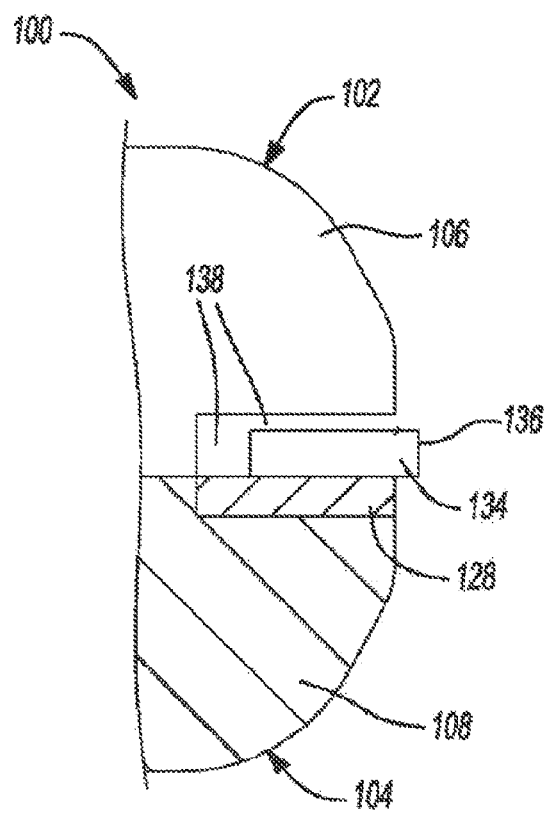
FIG. 10 is a cross-sectional view of a jaw assembly.

FIG. 10 illustrates a cross section of a jaw assembly 100 that is similar to the jaw assembly illustrated in FIG. 8. The jaw assembly 100 includes a first jaw 102 and a second jaw 104. The first jaw 102 includes a first jaw body 106. The second jaw 104 includes a second jaw body 108, a second insulator 128, and sealing plates 134. The insulator 128 has an edge or periphery 121 that extends beyond or overhangs an edge or periphery of the jaw bodies 106, 108. The sealing plates 134 has an edge or periphery 136 that extends beyond or overhangs an edge or periphery of the jaw bodies 106, 108, an edge or periphery 121 of the insulators 128, or both. The jaw assembly 100 of FIG. 10 can be used in one or more of the use states described in FIG. 8 above.

Figure 11:
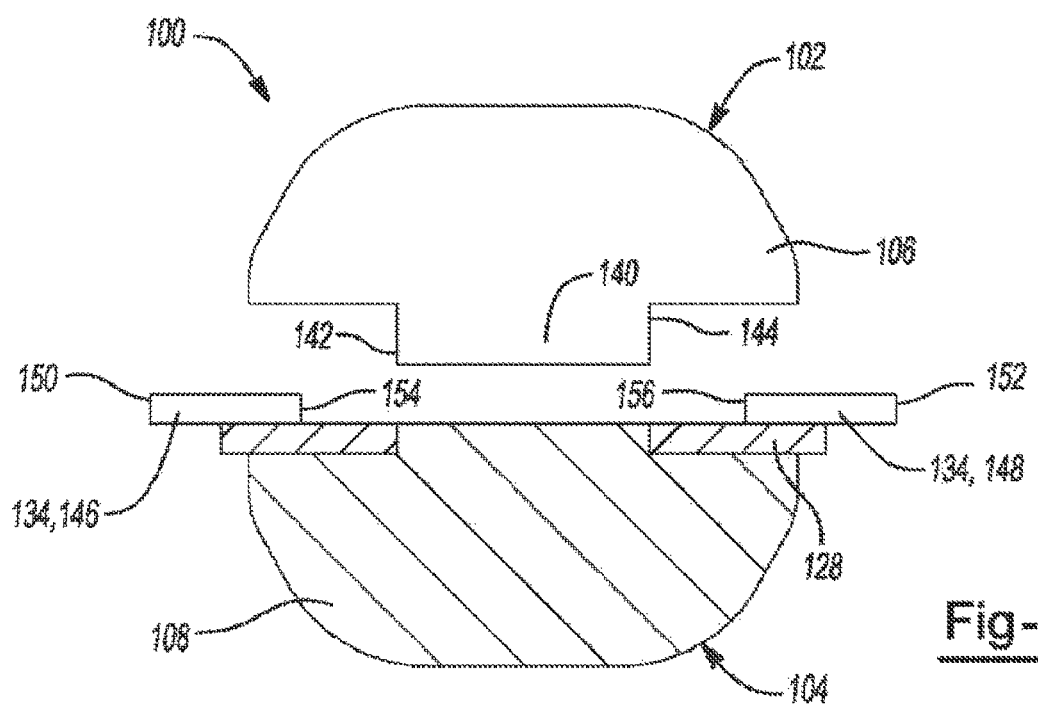
FIG. 11 is a cross-sectional view of a jaw assembly.

FIG. 11 illustrates a cross section of a jaw assembly 100. The jaw assembly 100 includes a first jaw 102 and a second jaw 104. The first jaw 102 includes a first jaw body 106 and a first electrode 140. The first electrode 140 may be integrally formed with the first jaw body 106 or may be separated from the first jaw body 106 via an insulator. The first electrode 140 may be a cutting element. The first electrode includes a first lateral edge 142 and a second lateral edge 144. The second jaw 104 includes a second jaw body 108, an insulator 128, and a sealing plate 134. The seating plate 134 includes a first arm 146 and a second arm 148. The first arm 146 and the second arm 148 may be individually or together connected to the power source 210. The first arm 146 and the second arm 148 may be electrically connected together. The sealing plate 134 or the first arm 146 includes a first lateral edge 150, and the sealing plate 134 or the second arm 148 includes a second lateral edge 152. The edges 150, 152 may be located within a periphery or edge of the first jaw body 106, the second jaw body 108, or both. The sealing plate 134 and/or the arms 146, 148 may be moveable so that the edges 150, 152 are located within an edge or periphery of the first and/or second jaw bodies 106, 108 and/or extend beyond an edge or periphery of the first and/or second jaw bodies 106, 108. The seating plate 134 or the first arm 146 includes a first interior edge 154, and the sealing plate 134 or the second arm 148 includes a second interior edge 156. A first gap is defined between the first interior edge 154 of the sealing plate 134 or first as 146 and the first lateral edge 142 of the first electrode 140. A second gap is defined between the first interior edge 154 of the sealing plate 134 or first arm 146 and the second interior edge 156 of the sealing plate 134 or the second arm 148. A third gap is defined between the second lateral edge 144 of the first electrode 140 and the second interior edge 156 of the sealing plate 134 or the second arm 148.

With continued reference to FIG. 11, the first jaw body 106 and/or the first electrode 140 and the second jaw body 108 have a first polarity (e.g. '−') and the sealing plate has 134 or arms 146, 148 have a second polarity (e.g. or vice versa. That is, the first jaw body 106 and/or the first electrode 140 and the second jaw body 110 are individually or together electrically connected to the first pole of a power source 210 (FIG. 13) and the sealing plate 134 or arms 146, 148 are electrically connected to a second pole of the power source 210, or vice versa.

With continued reference to FIG. 11, in a first use state, an object or anatomical feature can be surgically effected by placing the anatomical feature between the jaw bodies 106, 108 and passing a suitable therapy current between the sealing plates 134 and the first electrode 140 and/or the jaw bodies 106, 108.

With continued reference to FIG. 11, in a second use state, an object or anatomical feature can be surgically effected by moving or sweeping the jaw assembly 100 across the anatomical feature so that the edge or peripheries 150, 152 of the sealing plate 134 and/or arms 146, 148 contact the object or anatomical feature while a suitable therapy current is passed between the second sealing plate 134 or arms 146, 148 and the first electrode 140 and/or one or both of the jaw bodies 106, 108.

With continued reference to FIG. 11, in a third use state, a anatomical feature can be surgically effected by placing the anatomical feature between the jaw bodies 106, 108 and moving a cutting element 116 through the anatomical feature. The cutting element can be similar to the cutting element 116 of FIG. 7.

FIG. 12A illustrates a cross section of a jaw assembly 100. The jaw assembly 100 includes a first jaw 102 and a second jaw 104. The first jaw 102 includes a first jaw body 106, a first electrode 140, and an insulator 128. The first electrode 140 may be a cutting element. The first electrode includes a first lateral edge 142. The second jaw 104 includes a second jaw body 108, an insulator 128, and a sealing plate 134. The sealing plate 134 includes a first interior edge 154. A first gap is defined between the first interior edge 154 of the sealing plate 134 and the first lateral edge 142 of the first electrode 140. A lateral edge of the sealing plate 134 extends beyond an edge of the first jaw body 106 and the second jaw body 108. The sealing plate 134 may be moveable so that the first lateral edge extends under hangs or is generally flush with the edges of the jaw bodies 106, 108.

FIG. 12B illustrates a cross section of a jaw assembly 100 that may be substantially similar to the jaw assembly 100 shown in FIG. 12A except that the first electrode 140 is integrally formed with the first jaw body 106.

With reference to FIGS. 12A and 12B, the first jaw body 106 and/or the first electrode 140 and the second jaw body 108 have a first polarity (e.g. '−') and the sealing plate has 134 has a second polarity (e.g. '+'), or vice versa. That is, the first jaw body 106 and/or the first electrode 140 and the second jaw body 110 are individually or together electrically connected to the first pole of a power source 210 (FIG. 1) and the sealing plate 134 is electrically connected to a second pole of the power source 210, or vice versa.

With reference to FIGS. 12A and 12B, in a first use state, an object or anatomical feature can be surgically effected by placing the anatomical feature between the jaw bodies 106, 108 and passing a suitable therapy current between the sealing plate 134 and the first electrode 140 and/or the jaw bodies 106, 108.

With continued reference to FIGS. 12A and 12B, in a second use state, an object or anatomical feature can be surgically effected by moving or sweeping the jaw assembly 100 across the anatomical feature so that the edge or periphery of the sealing plate 134 and/or first electrode 140 contact the object or anatomical feature while a suitable therapy current is passed between the sealing plate 134, the first electrode 140 and/or one or both of the jaw bodies 106, 108, or a combination thereof.

With continued reference to FIGS. 12A and 12B in a third use state, a anatomical feature can be surgically effected by placing the anatomical feature between the jaw bodies 106, 108 and moving a cutting element through the anatomical feature. The cutting element can be similar to the cutting element 116 of FIG. 7.

FIG. 13 illustrates a medical device 200. The medical device 200 includes a hand piece 202 and an introducer 204. The hand piece 202 includes a gripping portion 206 and one or more user inputs 208 and mechanisms 212 within the hand piece 202 for manipulating a jaw assembly 100 extending from a distal end of the introducer 204. The medical device 200, the jaw assembly 100, the one or more jaws, jaw bodies, sealing members, electrodes, or a combination thereof may be in communication with a power source 210.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Teachings of a range in terms of at "'x' parts by weight of the resulting polymeric blend composition" also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it, be regarded that the inventors did not consider such subject matter to be part of the disclosed inventive subject matter.

The invention claimed is:

1. A medical device, comprising:
   a power source; and
   a bipolar forceps including a jaw assembly comprising:
   i. a first jaw comprising:
      a. a first jaw body electrically connected to a first pole of the power source and having a first polarity;
      b. a sealing plate electrically connected to the first pole of the power source and having the first polarity; and
      c. an insulator electrically isolating the first jaw body from the sealing plate;
      wherein the sealing plate, the insulator, and the first jaw body are sequentially stacked in a direction of height extending from an inner tissue engaging surface of the first jaw to an outer surface of the first jaw;

ii. a second jaw comprising:
a. a second jaw body electrically connected to a second pole of the power source and having a second polarity;

wherein in a first use state, an anatomical feature is surgically affected between the sealing plate and the second jaw body by passing a therapy current between the sealing plate and the second jaw body, and wherein in a second use state an anatomical feature is surgically affected by moving the first and second jaws to a closed configuration, contacting the anatomical feature with an edge of the sealing plate and passing a therapy current between the first jaw body and the second jaw body.

2. The medical device according to claim 1, wherein the second jaw body comprises a sealing surface, and the sealing surface comprises one or more insulators.

3. The medical device according to claim 2, wherein the sealing surface comprises a cutting recess, and the medical device comprises a cutting element located within the cutting recess.

4. The medical device according to claim 3, wherein the second jaw body comprises an insulator located on a side of the second jaw body that opposes the sealing surface.

5. The medical device according to claim 2, wherein the second jaw body comprises an insulator located on a side of the second jaw body that opposes the sealing surface.

6. The medical device according to claim 1, wherein the second jaw body comprises a cutting recess, and the medical device comprises a cutting element located within the cutting recess.

7. The medical device according to claim 1, wherein the second jaw body comprises a sealing surface disposed on one side of the second jaw body and an insulator disposed on an opposite side of the second jaw body.

8. A medical device, comprising:
a power source; and
a bipolar forceps including a jaw assembly comprising:
i. a first jaw comprising:
a. a first jaw body electrically connected to a first pole of the power source and having a first polarity;
b. a first sealing plate electrically connected to a second pole of the power source and having a second polarity; and
c. a first insulator electrically isolating the first jaw body and the first sealing plate;
ii. a second jaw comprising:
a. a second jaw body electrically connected to the first pole of the power source and having the first polarity;
b. a second sealing plate electrically connected to the first pole of the power source and having the first polarity; and
c. a second insulator electrically isolating the second jaw body and the second sealing plate;

wherein in a first use state, the first sealing plate and the second sealing plate have opposing polarities so that an anatomical feature is surgically affected between the first sealing plate and the second sealing plate, wherein in a second use state, the first sealing plate has a polarity that is opposite a polarity of the first jaw body and the second jaw body so that an anatomical feature is surgically affected with an edge of the first sealing plate, and wherein a profile of the first sealing plate or a profile of the second sealing plate is entirely encompassed within a profile of the first jaw body or a profile of the second jaw body.

9. The medical device of claim 8, wherein both the first jaw body and the second jaw body comprise a bulk conductive material.

10. The medical device of claim 8, wherein the first sealing plate, the second sealing plate or both include at least one insulating spacer that prevents the first sealing plate and the second sealing plate from making contact.

11. The medical device of claim 8, wherein a profile of the second sealing plate is located within a profile of the first sealing plate.

12. The medical device of claim 8, wherein at least a portion of the first sealing plate is reconfigurable so that the edge of the first sealing plate substantially matches an edge of the second sealing plate.

13. The medical device of claim 8, wherein at least a portion of the first sealing plate is reconfigurable so that the edge of the first sealing plate is made to extend beyond an edge of the second sealing plate.

14. The medical device of claim 8, wherein the second jaw body comprises a cutting recess and the medical device comprises a cutting element located within the cutting recess.

15. A medical device, comprising:
a bipolar forceps including a jaw assembly comprising:
i. a first jaw comprising:
a. a first jaw body;
b. a sealing plate; and
c. an insulator electrically isolating the first jaw body from the sealing plate;
wherein the sealing plate, the insulator, and the first jaw body are sequentially stacked in a direction of height extending from an inner tissue engaging surface of the first jaw to an outer surface of the first jaw;
ii. a second jaw comprising:
a. a second jaw body including a sealing surface, the sealing surface including one or more insulators having an exposed insulator surface that is oriented toward the sealing plate;

wherein in a first use state, an anatomical feature is surgically affected between the sealing plate and the second jaw body by passing a therapy current between the sealing plate and the second jaw body, and wherein in a second use state an anatomical feature is surgically affected by contacting the anatomical feature with an edge of the sealing plate and passing a therapy current between the first jaw body and the second jaw body.

16. The medical device of claim 15, wherein the second jaw body comprises a cutting recess, and the medical device comprises a cutting element located within the cutting recess.

17. The medical device of claim 15, wherein the second jaw body comprises an insulator located on a side of the second jaw body that opposes the sealing surface.

18. The medical device of claim 15, wherein the exposed insulator surface of the one or more insulators extends through the sealing surface of the second jaw body.

* * * * *